United States Patent [19]

Fawzi

[11] 4,343,798
[45] Aug. 10, 1982

[54] TOPICAL ANTIMICROBIAL ANTI-INFLAMMATORY COMPOSITIONS

[75] Inventor: Mahdi B. Fawzi, Fairfield, Ohio

[73] Assignee: The Procter & Gamble Company, Cincinnati, Ohio

[21] Appl. No.: 276,556

[22] Filed: Jun. 23, 1981

[51] Int. Cl.³ .............................................. A01N 45/00
[52] U.S. Cl. ..................................................... 424/240
[58] Field of Search ......................................... 424/240

[56] References Cited

U.S. PATENT DOCUMENTS 2,466,663  4/1949  Russ et al. .................. 260/397.45
4,018,918  4/1977  Ayer et al. .......................... 424/240
4,124,720  11/1978  Wenmaekers ...................... 424/240

FOREIGN PATENT DOCUMENTS 2912438  10/1980  Fed. Rep. of Germany ...... 424/240

OTHER PUBLICATIONS

Raab, Dermatologica, 152 (suppl. 1), 67–79 (1976).
Raab, Br. J. Derm., 84 582 (1971).
Keeney, Bull. Johns Hopkins Hosp. 78, 33 (1946).
Dobozy, et al., Hautarzt, 1976 (Suppl. 1) 11–13.
Raab, et al., Chemotherapy 15 (1), 26–34 (1970).
Raab, Acta. Derm – Vernerol., Suppl. 52 (67), 32–39 (1972).
Zygmunt, et al., Appl. Microbiol. 14(6), 856 (1966).

Primary Examiner—Elbert L. Roberts
Attorney, Agent, or Firm—Steven J. Goldstein; Jack D. Schaeffer; Richard C. Witte

[57] ABSTRACT

Topical antimicrobial anti-inflammatory compositions, having a pH no greater than about 5, containing $C_5$–$C_{12}$ fatty acids together with a corticosteroid component, are disclosed. The method of topically treating inflammatory skin conditions using these compositions is also disclosed.

16 Claims, No Drawings

TOPICAL ANTIMICROBIAL ANTI-INFLAMMATORY COMPOSITIONS

TECHNICAL FIELD

The present invention relates to topical pharmaceutical compositions which provide both antimicrobial and anti-inflammatory benefits.

BACKGROUND OF THE INVENTION

The administration of corticosteroids to treat inflamed tissue is an important and widely-used treatment modality, especially in dermatology. Since topical corticosteroids can act to depress local antimicrobial defenses, it would be very helpful to be able to use such compounds together with antimicrobial agents in the topical treatment of skin disorders. See, Raab, *Dermatologica*, 152 (Suppl. 1), 67-79 (1976) and Raab, *Br. J. Derm.*, 84, 582 (1971). $C_5$-$C_{12}$ carboxylic acids, especially caprylic (octanoic) acid, are lipophilic materials known in the art to be effective, broad spectrum antimicrobial agents which may be used topically. See, Keeney, *Bull. Johns Hopkins Hosp.*, 78, 333 (1946); U.S. Pat. No. 2,466,663, Russ, et al., issued Apr. 5, 1949; and U.S. patent application Ser. No. 918,532, Stone, filed June 23, 1978.

It is well-known in the pharmaceutical arts that negative interactions can occur when certain types of antimicrobial agents, especially lipophilic antimicrobials, are used together with corticosteroids in combination therapy. Thus, for example, Dobozy, et al., *Hautarzt*, 1976 (Suppl. 1), 11-13, teach that percutaneous absorption of topical salves containing the lipophilic compounds oxytetracycline, clortetracycline and doxycycline is inhibited by the addition of glucocorticoids, such as prednisolone, hydrocortisone-17-butyrate, betamethasone valerate and dexamethasone pivalate. Raab, et al., *Chemotherapy*, 15 (1), 26-34 (1970), indicate that the corticosteroids cortisol, methyl prednisolone hemisuccinate and fluocinolone acetonide significantly reduce the antibacterial activity of dodecyldi(beta-hydroxyethyl)benzylammonium chloride and dodecyl triphenylphosphonium bromide (both of which are lipophilic compounds). Raab, *Acta. Derm.-Venereol., Suppl.* 52 (67), 32-39 (1972), teaches that fluocinolone acetonide acetate causes a decrease in the fungicidal activity of 1-p-chlorobenzyl-2-methylbenzimidazole and the bactericidal activity of dodecyldi(betahydroxyethyl)-benzylammonium chloride; yet, there is no impairment of microbiological activity noted when non-lipophilic antimicrobials, such as nystatin, natamycin, or neomycin, are combined with fluocinolone acetonide. Finally, Zygmunt, et al., *Appl. Microbiol.*, 14(6), 865 (1966) disclose a wide range of steroid interference with the antifungal activity of a group of lipophilic polyene antibiotics.

Thus, based on the art, one would have expected negative interactions when corticosteroids were used together with lipophilic $C_5$-$C_{12}$ fatty acid antimicrobial agents in combination therapy. Yet, surprisingly, it has now been found that such combinations can be made, exhibiting outstanding anti-inflammatory and antimicrobial efficacy, without any negative interactions.

Accordingly, it is an object of the present invention to provide effective topical antimicrobial and anti-inflammatory compositions containing $C_5$-$C_{12}$ fatty acids and corticosteroid components.

It is a further object of the present invention to provide a method for the effective topical treatment of inflammatory skin disorders.

SUMMARY OF THE INVENTION

The present invention provides topical pharmaceutical compositions, having a pH of no greater than about 5, comprising a safe and effective amount of an antimicrobial agent selected from $C_5$-$C_{12}$ fatty acids (especially octanoic or decanoic acid) and mixtures thereof, together with a safe and effective amount of a corticosteroid component, preferably triamcinolone acetonide, hydrocortisone acetate, betamethasone valerate, or fluocinolone acetonide.

In another aspect, the present invention provides a method for treating inflammatory skin conditions in humans or animals wherein a safe and effective amount of the composition described above is topically applied to the afflicted situs.

DETAILED DESCRIPTION OF THE INVENTION

The phrase "safe and effective amount", as used herein, means a sufficient amount of fatty acid, corticosteroid, or topical composition, to provide the desired antimicrobial and/or anti-inflammatory performance, at a reasonable benefit/risk ratio attendant with any medical treatment. Within the scope of sound medical judgement, the required dosage of fatty acid or corticosteroid will vary with the nature and severity of the condition being treated, the duration of the treatment, the nature of adjunct treatment, the age and physical condition of the patient, the specific fatty acid and corticosteroid compounds employed, and like considerations discussed more fully hereinafter.

"Pharmaceutically-acceptable", as used herein, means that the fatty acid and corticosteroid compounds, as well as other ingredients used in the compositions of the present invention, are suitable for use in contact with the tissues of humans and lower animals without undue toxicity, irritation, allergic response, and the like, commensurate with a reasonable benefit/risk ratio.

The term "comprising", as used herein, means that various other compatible drugs and medicaments, as well as inert ingredients, can be conjointly employed in the therapeutic compositions of this invention, as long as the critical fatty acid and corticosteroid components are used in the manner disclosed. The term "comprising" thus encompasses and includes the more restrictive terms "consisting of" and "consisting essentially of".

By "compatible" herein is meant that the components of the compositions of this invention are capable of being commingled without interacting in a manner which would substantially decrease the efficacy of the fatty acid or corticosteroid compounds under ordinary usage conditions.

All percentages and ratios used herein are by weight, unless otherwise specified.

The fatty acids useful in the present invention contain from 5 to 12 carbon atoms; compounds outside of this range exhibit significantly less antimicrobial efficacy. These materials, themselves, are well-known in the art. For example, octanoic acid is an oily liquid having a boiling point of 239.7° C. and a melting point of 16.7° C.; it is very slightly soluble in water (0.068 g/100 g at 20° C.) and freely soluble in alcohol, chloroform, carbon disulfide, petroleum ether and glacial acetic acid. Octanoic acid may be prepared from 1-heptene, Dupont, et al., Compt. Rend. 240, 628 (1955), or by the oxidation of octanol, Langenbeck, et al., Ber. 89, 202 (1956). The manufacture of octanoic acid is described in U.S. Pat. No. 2,821,534, issued in 1958 and assigned to GAF, and U.S. Pat. No. 3,053,869, issued in 1960 and assigned to Standard Oil of Indiana. See also Fatty Acids, Part 1, K. S. Markley, ed. (Interscience, New York, 2d edition, 1960) pages 34, 38. Decanoic acid is a crystalline solid having a melting point of 31.4° C.; it is practically insoluble in water. See Fatty Acids, Part 1, supra, pages 34, 39. Decanoic acid may be prepared from octyl bromide, Shishido, et al., J. Am. Chem. Soc. 81, 5817 (1959), and U.S. Pat. No. 2,918,494, issued in 1959 and assigned to Ethyl Corporation.

It is preferred that the fatty acid component be a $C_5-C_{12}$ non-aromatic carboxylic acid, such as n-pentanoic acid, n-hexanoic acid, n-heptanoic acid, n-octanoic acid, n-nonanoic acid, n-decanoic acid, n-undecanoic acid, or n-dodecanoic acid. Preferred fatty acids contain from 6 to 10 carbon atoms, with octanoic acid and decanoic acid being especially preferred. Mixtures of theses acids may also be used, as well as the acid salts, provided that the pH criteria for the entire compositions are met. The fatty acid components are included in the compositions of the present invention in a safe and effective amount, preferably comprising from about 0.5% to about 20%, more preferably from about 1% to about 10%, of the completed compositions.

The compositions of the present invention are formulated such that they have a pH no greater than about 5, preferably no greater than about 4, most preferably between about 3 and 4. At pH's greater than 5, antimicrobial performance of the composition falls off significantly; obviously, a pH which is too low (acidic) would not be suitable for topical use. Compatible acidic or basic ingredients may be used in order to adjust the composition pH to the desired range.

The corticosteroid components useful in the present invention are well-known in the pharmaceutical arts and are described in detail in Miller and Munro, Drugs, 19, 119–134 (1980), incorporated herein by reference. The essential steroid structure consists of 17 carbon atoms, arranged in four rings, 3 six-membered rings and 1 five-membered ring (see Chart 1, below). Since this is a rigid structure, small changes in the position of substitutents can lead to significant changes in biological activity, presumably as a consequence of interactions with specific receptors.

Chart 1

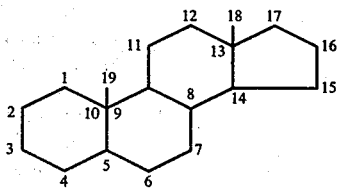

Basic steroid structure

-continued
Chart 1

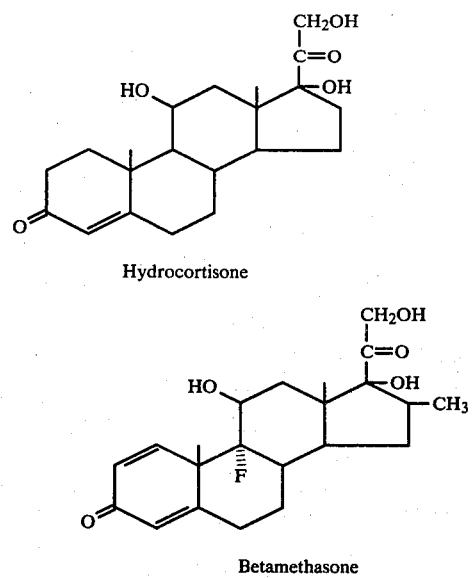

Hydrocortisone

Betamethasone

The anti-inflmmatory steroids were developed by various modifications of this basic nucleus, for example:
(1) The introduction of a 1:2 double bond into hydrocortisone both increased glucocorticoid activity (by approximately 4 times) and reduced mineralocorticoid effects. prednisone and prednisolone resulted.
(2) The synthesis of the 9 alpha-halogenated derivatives had a large effect on glucocorticoid activity, but also enhanced mineralocorticoid properties. This latter problem was counteracted by further substitution at the 16 position with an alpha-hydroxyl (triamcinolone), alphamethyl(dexamethasone) or beta-methyl(betamethasone) group.

Other modifications in the molecular structure could possibly have the effect of removing some of the remaining undesirable side effects or enhancing the positive effects of the corticosteroids. Changes in these systemically active anti-inflammatory steroids to improve lipophilicity (i.e., increased fat solubility relative to that in water) greatly improved their topical effectiveness. This generally involves masking or removing hydroxyl groups or the introduction of long carbon side chains.

Examples of specific corticosteroids and their customary dosage levels useful in the present invention can be broken down into four classes:
(1) Very potent
Beclomethasone dipropionate 0.5%
Clobetasol propionate 0.05%
Diflucortolone valerate 0.3%
Fluocinolone acetonide 0.2%
(2) Potent
Beclomethasone dipropionate 0.025%
Betamethasone benzoate 0.025%
Betamethasone dipropionate 0.05%
Betamethasone valerate 0.1%
Desonide 0.05%
Desoxymethasone 0.25%
Diflorasone diacetate 0.05%
Diflucortolone valerate 0.1%
Fluclorolone acetonide 0.025%

Fluocinolone acetonide 0.025%
Fluocinonide 0.05%
Fluocortolone 0.5%
Fluprednidene (fluprednylidene) acetate 0.1%
Flurandrenolone 0.05%
Halcinonide 0.1%
Hydrocortisone butyrate 0.1%
Triamcinolone acetonide 0.1%
(3) Moderately Potent
Clobetasone butyrate 0.05%
Flumethasone pivalate 0.02%
Fluocinolone acetonide 0.01%
Flucortin butylester 0.75%
Flucortolone 0.2%
Flurandrenalone 0.0125%–0.025%
Hydrocortisone with urea 1%
(4) Mild
Dexamethasone 0.01%
Hydrocortisone (alcohol or acetate) 0.1%–1%
Methylprednisolone 0.25%

Mixtures of corticosteroids are also useful in the present invention. Particularly preferred corticosteroids for use in the present invention include triamcinolone acetonide, hydrocortisone acetate, betamethasone valerate, fluocinolone acetonide, and mixtures thereof. Compositions of the present invention contain a safe and effective amount of the corticosteroid component; preferably the compositions contain from about 0.01% to about 10%, more preferably from about 0.02% to about 5%, of corticosteroid.

The compositions of the present invention may additionally contain adjunct components conventionally found in pharmaceutical compositions in their art-established usage levels. Thus, for example, the compositions may contain additional compatible pharmaceutically-active materials for combination therapy (such as supplementary antimicrobials, antipruritics, astringents, local anaesthetics, or non-steroidal anti-inflammatory agents), or may contain materials useful in physically formulating various dosage forms of the present invention, such as excipients, dyes, perfumes, thickening agents, stabilizers, skin penetration enhancers, preservatives, or antioxidants. The balance of the compositions of the present invention may also contain, in an amount which can range from about 1% to about 99.5% of the compositions, compatible pharmaceutical carrier materials, generally in liquid or semi-liquid form, especially adapted for topical application. It is desirable that the carrier selected be capable of codissolving the materials used in the composition. Carrier materials suitable for use in the instant composition include those well-known for use in the cosmetic and medical arts as a basis for ointments, lotions, creams, salves, aerosols, suppositories, gels and the like. A particularly preferred composition of the present invention is formulated as an aqueous lotion or an aqueous gel, containing at least about 15% water; the preferred aqueous gels, also contain an acidic carboxy polymer as the gelling agent. Such lotion and gel compositions are described in concurrently-filed U.S. patent application Ser. No. 276,557, Fawzi, entitled "Topical Antimicrobial Compositions", incorporated herein by reference. Suitable carriers include, for example, water, liquid alcohols, liquid glycols, liquid polyalkalene glycols, liquid esters, liquid amides, liquid protein hydrolysates, liquid alkalated protein hydrolysates, liquid lanolin and lanolin derivatives, and like materials. Exemplary carriers include both monohydric and polyhydric alcohols, for example ethanol, isopropanol, glycerol, sorbitol, 2-methoxy ethanol, diethylene glycol, ethylene glycol, hexalene glycol, mannitol, and propylene glycol; ethers, such as diethyl or dipropyl ether; polyethylene glycols and methoxy polyoxyethylenes (such as carbowaxes having molecular weights ranging from 200 to 20,000); polyoxyethylene glycerols, polyoxyethylene sorbitols, and stearoyl diacetin. Oil-in-water emulsions, such as cold cream bases, can also be used.

Topical treatment regimens according to the practice of this invention comprise applying the compositions herein directly to the skin, i.e., at the situs of an inflammatory skin disorder. The compositions may also be formulated for use in the oral or vaginal cavities. The rate of application and duration of treatment will, of course, depend on the severity and nature of the condition being treated, the response, and physical condition of the particular patient, and related factors within the sound medical judgement of the attending physician. In general, for the compositions of the present invention, application rates of from about 5 milligrams/cm$^2$ to about 100, preferably from about 5 to about 50, milligrams/cm$^2$ per day are used. Application can be made once, or preferably several times, daily for periods of a week or more. Conditions usefully treated with the compositions of the present invention include, but are not limited to, cutaneous candidiasis; superficial bacterial infections; the following conditions when complicated by candidal and/or bacterial infection: dermatitis (atopic, eczematoid, stasis, nummular, contact, or seborrheic), neurodermatitis, and dermatitis venenate; pruritus ani; pruritus vulvae; infantile eczema; and lichen simplex chronicus. In addition, the present invention may be formulated and used in a veterinary context, for example in the treatment of dermatological disorders characterized by inflammation and dry or exudative dermatitis, eczematous dermatitis, contact dermatitis, seborrheic dermatitis, and as an adjunct in the treatment of dermatitis due to parasitic infestation.

The following examples illustrate the content, preparation and use of topical compositions of this invention, but are not intended to be limiting thereof.

EXAMPLE I

The antimicrobial efficacy of aqueous gel formulations of the present invention was compared to that of similar compositions formulated as creams, ointments and non-aqueous gels, using an in vitro disk diffusion test procedure. In this procedure, filter paper disks (11–13 mm diameter) were coated with the compositions to be tested and placed on top of agar media containing the microorganisms of interest. The agar was incubated (under conditions dictated by the particular microorganisms being used) overnight to allow the microorganisms to grow. As the test formulation diffused from the disk out through the agar, the growth of the microorganism was inhibited. Clear zones of inhibition were formed around the disks and were measured the following day. The size of the zone represents the degree of antimicrobial activity of the particular composition. The antimicrobial efficacy of the compositions was tested against Candida albicans (Candida), Staphylococcus aureus (Staph) and Pseudomonas aeruginosa (Pseudo). The compositions were tested both with and without a layer of synthetic sebum spread over the surface of the agar.

The compositions tested are summarized in the following table.

| Composition | Octanoic Acid | Triamcinolone Acetonide |
|---|---|---|
| 1 (aqueous gel) | 4% | 0.1% |
| 2 (cream) | 4% | 0.1% |
| 3 (ointment) | 4% | 0.1% |
| 4 (non-aqueous gel) | 4% | 0.1% |
| 5 (aqueous gel) | 4% | — |
| 6 (non-aqueous gel) | 4% | — |
| 7 (ointment) | 4% | — |
| 8 (cream) | 4% | — |

All compositions had a pH between about 3 and 4. The aqueous gel compositions included (vehicle) 1% myristyl alcohol; 25% propylene glycol; 5% Pluronic L-64; 1% beta-alanine; 25% of 4% aqueous Carbopol 934; with the balance being water. Conventional cream, ointment and non-aqueous gel bases were used for the remaining compositions. The antimicrobial performance of these compositions is given in the following table.

| | Zones of Inhibition (mm) | | | | | | | |
|---|---|---|---|---|---|---|---|---|
| | 1 | 2 | 3 | 4 | 5 | 6 | 7 | 8 |
| Candida | | | | | | | | |
| sebum | 29 | 22 | 19 | 18 | 26 | 19 | 21 | 23 |
| no sebum | 45 | 37 | 30 | 24 | 42 | 26 | 30 | 35 |
| Staph | | | | | | | | |
| sebum | 21 | 19 | 17 | 15 | 21 | 16 | 16 | 19 |
| no sebum | 33 | 32 | 24 | 20 | 34 | 20 | 24 | 30 |
| Pseudo | | | | | | | | |
| no sebum | 42 | 31 | 23 | 20 | 39 | 20 | 25 | 32 |

These data indicate that the compositions when formulated as aqueous gels of the present invention demonstrate clear antimicrobial performance advantages over similar compositions formulated as creams, ointments or non-aqueous gels.

Substantially similar results are obtained where the aqueous gel formulations, described above, are formulated as aqueous lotions by eliminating the Carbopol gelling agent.

Substantially similar results are also obtained where the octanoic acid in the above compositions is replaced, in whole or in part, with pentanoic, hexanoic, heptanoic, nonanoic, decanoic, undecanoic or dodecanoic acid, or mixtures thereof.

Similar results are also obtained where the triamcinolone acetonide in the above compositions is replaced, in whole or in part, with beclomethasone dipropionate, clobetasol propionate, diflucortolone valerate, fluocinolone acetonide, betamethasone benzoate, betamethasone dipropionate, betamethasone valerate, desonide, desoxymethasone, diflorasone diacetate, fluclorolone acetonide, fluocinonide, fluocortolone, fluprednidene (fluprednylidene) acetate, flurandrenolone, halcinonide, hydrocortisone butyrate, clobetasone butyrate, flumethasone pivalate, fluocortin butylester, hydrocortisone with urea, dexamethasone, hydrocortisone alcohol or acetate, methylprednisolone, or mixtures thereof.

EXAMPLE II

Using the disk diffusion procedure described in Example I, the antimicrobial efficacy of compositions of the present invention was tested. All of the compositions had pH's in the range of from 3 to 4. The compositions tested are described in the table below; in addition to the listed components all of the compositions were formulated as aqueous gels, containing 1% myristyl alcohol, 25% propylene glycol, 5% Pluronic L-64, 25% of 4% Carbopol 934 gelling agent, with the balance of the compositions being water.

| | Composition (weight %) | | | | | |
|---|---|---|---|---|---|---|
| Components | 1 | 2 | 3 | 4 | 5 | 6 |
| Octanoic Acid | — | — | — | — | 4.0 | 4.0 |
| Decanoic Acid | 4.0 | 4.0 | 6.0 | 6.0 | — | — |
| Triamcinolone Acetonide | 0.1 | 0.1 | 0.1 | 0.1 | 0.1 | 0.1 |
| Beta-alanine | 1.0 | — | 1.0 | — | 1.0 | — |
| 1 N NaOH | — | 7.0 | — | 7.0 | — | 7.0 |

The antimicrobial performance of each of these compositions, expressed as zone of inhibition diameters, over a range of gram positive and gram negative bacteria, both in the presence and absence of sebum, is summarized in the following table.

| | Zones of Inhibition (mm) | | | | | |
|---|---|---|---|---|---|---|
| | 1 | 2 | 3 | 4 | 5 | 6 |
| Staph | | | | | | |
| no sebum | 25 | 24 | 27 | 27 | 30 | 31 |
| sebum | 16 | 16 | 16 | 18 | 21 | 22 |
| Candida | | | | | | |
| no sebum | 21 | 21 | 24 | 20 | 38 | 38 |
| sebum | 0 | 0 | 0 | 0 | 28 | 25 |
| Pseudo | | | | | | |
| no sebum | 25 | 18 | 25 | 17 | 30 | 23 |

Similar results are obtained where the aqueous gel compositions, described above, are formulated without the Carbopol gelling agent, yielding aqueous lotion compositions.

EXAMPLE III

Using conventional pharmaceutical formulational techniques, antimicrobial compositions described in the following table were formulated as aqueous gels; each composition had a pH below 5.

| | Composition (weight %) | | | | | | | | |
|---|---|---|---|---|---|---|---|---|---|
| Components | 1 | 2 | 3 | 4 | 5 | 6 | 7 | 8 | 9 |
| Octanoic Acid | 4.0 | → | → | → | → | → | → | → | → |
| Monolauren | 1.0 | → | → | → | → | → | → | → | → |
| Pluronic L-64[1] | 5.0 | | | | | 5.0 | | | |
| Pluronic F-108 | | | | 2.4 | | | | | |
| Pluronic F-127 | | 5.0 | | 2.5 | | | 5.0 | | 2.5 |
| Pluronic F-123 | | | 5.0 | 2.5 | | | | 5.0 | 2.5 |
| Pluronic L-122 | | | | | 2.6 | | | | |
| Propylene glycol | 20.0 | → | → | → | → | | | | |
| Glycerin | | | | | | 20.0 | 20.0 | 20.0 | 20.0 |
| 1 N NaOH | 7.5 | → | → | → | → | → | → | → | → |
| Carbopol 934[2] | 1.0 | → | → | → | → | → | → | → | → |
| Water | 61.5 | → | → | → | → | → | → | → | → |

| Components | 10 | 11 | 12 | 13 | 14 | 15 | 16 | 17 |
|---|---|---|---|---|---|---|---|---|
| Octanoic Acid | 4.0 | → | → | → | → | → | → | → |
| Monolauren | 1.0 | → | → | → | → | → | | |
| Pluronic L-64[1] | | 5.0 | | | | | | |
| Pluronic F-108 | 2.4 | | | | 2.4 | | | 2.4 |
| Pluronic F-127 | | | 5.0 | | 2.5 | | 5.0 | |
| Pluronic F-123 | | | | 5.0 | 2.5 | | | |
| Pluronic L-122 | 2.6 | | | | | 2.6 | | 2.6 |
| Propylene glycol | | 10.0 | → | → | → | → | → | → |
| Glycerin | 20.0 | 10.0 | → | → | → | → | → | → |
| 1 N NaOH | 7.5 | → | → | → | → | → | → | → |
| Carbopol 934[2] | 1.0 | → | → | → | → | → | → | → |

| Composition (weight %) | | | | | | | |
|---|---|---|---|---|---|---|---|
| Water | 61.5 | → | → | → | → | 62.5 | 62.5 |

[1]Pluronics are a series of nonionic block-copolymer condensates of ethylene oxide with hydrophobic bases formed by condensing propylene oxide with propylene glycol, commercially available from Wyandotte Chemicals Corporation. For example, Pluronic L-64 has a molecular weight of about 2900 and an HLB of 15.0. Pluronic F-108 has a molecular weight of about 14,000.
[2]Carbopol 934 is a polyacrylic acid polymer available from B. F. Goodrich; it is soluble in water, polar solvents and many non-polar solvent blends.

These compositions, when applied topically to an adult human, in an amount of about 8 milligrams/cm$^2$, are effective antimicrobial agents. Using the disk diffusion procedure, described above, each of these compositions has been shown to be effective against Staphylococcus epidermidis, Propionibacterium acnes, Candida albicans, and Pseudomonas aeruginosa. Similar results are also obtained when a corticosteroid selected from the group triamcinolone acetonide, hydrocortisone acetate, betamethasone valerate, fluocinolone acetonide, and mixtures thereof is added to any of these compositions in an amount constituting about 0.025% to about 0.5% of the final composition.

EXAMPLE IV

Using the disk diffusion method, described in Example I, aqueous gel, cream, ointment and non-aqueous gel compositions, having the formulae given in the following table, were screened for their antimicrobial effectiveness. All of the compositions tested had pH's below 5. The aqueous gel compositions contained 1% myristyl alcohol, 25% propylene glycol, 5% Pluronic L-64, 1% beta-alanine, 25% of 4% Carbopol 934, with the balance being water. Conventional cream, ointment and non-aqueous gel bases were used in formulating the remaining compositions.

| | Compositions (weight %) | | |
|---|---|---|---|
| | Octanoic Acid | Triamcinolone Acetonide | Decanoic Acid |
| 1 (aqueous gel) | 4 | — | — |
| 2 (aqueous gel) | 4 | 0.1 | — |
| 3 (cream) | 4 | — | — |
| 4 (cream) | 4 | 0.1 | — |
| 5 (ointment) | 4 | — | — |
| 6 (ointment) | 4 | 0.1 | — |
| 7 (aqueous gel) | — | — | 4 |
| 8 (aqueous gel) | — | 0.1 | 4 |
| 9 (aqueous gel) | — | 0.1 | 4 |
| 10 (aqueous gel) | — | — | 4 |
| 11 (non-aqueous gel) | — | 0.1 | 4 |
| 12 (non-aqueous gel) | — | — | 4 |

The results of these tests are summarized in the following table. These data indicate that the addition of triamcinolone acetonide to the octanoic acid and decanoic acid aqueous gel, cream, ointment or non-aqueous gel compositions resulted in no antagonistic effects on their antimicrobial activity.

| | Zones of Inhibition (mm) | | | | |
|---|---|---|---|---|---|
| | Candida | | Staph | | Pseudo |
| | sebum | no sebum | sebum | no sebum | no sebum |
| 1 | 26 | 42 | 21 | 33 | 39 |
| 2 | 29 | 45 | 22 | 34 | 42 |
| 3 | 23 | 35 | 19 | 30 | 32 |
| 4 | 22 | 37 | 19 | 32 | 30 |
| 5 | 21 | 30 | 17 | 24 | 25 |
| 6 | 19 | 30 | 17 | 23 | 23 |
| 7 | 19 | 26 | 16 | 20 | 20 |
| 8 | 18 | 24 | 15 | 20 | 20 |
| 9 | 0 | 28 | 15 | 32 | 39 |
| 10 | 0 | 20 | 16 | 31 | 29 |
| 11 | 0 | 0 | 0 | 15 | 0 |
| 12 | 0 | 0 | 0 | 15 | 0 |

Substantially similar results are obtained where the octanoic or decanoic acids of the above compositions are replaced, in whole or in part, with equivalent amounts of pentanoic, hexanoic, heptanoic, nonanoic, undecanoic or dodecanoic acid, or mixtures thereof. Similar results are also obtained where the triamcinolone acetonide is replaced, in whole or in part, with effective amounts of hydrocortisone acetate, betamethasone valerate, fluocinolone acetonide, beclomethasone dipropionate, clobetasol propionate, diflucortolone valerate, betamethasone benzoate, betamethasone dipropionate, desonide, desoxymethasone, diflorasone diacetate, fluclorolone acetonide, fluocinonide, fluocortolone, fluprednidene (fluprednylidene) acetate, flurandrenooone, halcinonide, hydrocortisone butyrate, clobetasone butyrate, flumethasone pivalate, fluocortin butylester, hydrocortisone with urea, dexamethasone, hydrocortisone alcohol or acetate, methylprednisolone, or mixtures thereof.

EXAMPLE V

In order to compare the antimicrobial activity of octanoic acid/triamcinolone acetonide combinations against the activity of compositions containing three other corticosteroids at concentrations which are common in currently marketed products, the following compositions were screened using the disk diffusion procedure. All of the compositions were in the form of aqueous gels; these gel compositions contained (vehicle) 1% myristyl alcohol, 25% propylene glycol, 5% Pluronic L-64, 1% beta-alanine, 25% of 4% aqueous Carbopol 934, with the balance being water. All of the gel compositions had pH's between about 3 and 4.

Compositions (weight %)

1—0.05% triamcinolone acetonide
2—0.05% triamcinolone acetonide+4% octanoic acid
3—0.5% hydrocortisone-21-acetate
4—0.5% hydrocortisone-21-acetate+4% octanoic acid
5—0.1% betamethasone valerate
6—0.1% betamethasone valerate+4% octanoic acid
7—0.025% fluocinolone acetonide
8—0.025% fluocinolone acetonide+4% octanoic acid
9—vehicle (no active)

The results of these experiments are summarized in the table, below. In all instances, the corticosteroid alone showed no antimicrobial activity. All of the compositions containing 4% octanoic acid showed good activity. Zones of inhibition were approximately the same size for all of these compositions regardless of the steroid or its concentration.

| | Zones of Inhibition (mm) | | | | |
|---|---|---|---|---|---|
| | Staph | | Candida | | Pseudo |
| | sebum | no sebum | sebum | no sebum | no sebum |
| 1 | 0 | 0 | 0 | 0 | 32 |
| 2 | 21 | 34 | 25 | 40 | 39 |
| 3 | 0 | 0 | 0 | 0 | 31 |
| 4 | 23 | 35 | 27 | 39 | 39 |
| 5 | 0 | 0 | 0 | 0 | 29 |
| 6 | 20 | 36 | 25 | 46 | 38 |
| 7 | 0 | 0 | 0 | 0 | 30 |
| 8 | 22 | 37 | 27 | 44 | 38 |
| 9 | 0 | 0 | 0 | 0 | 29 |

EXAMPLE VI

The croton oil mouse ear assay was used to assess the topical anti-inflammatory activity of the compositions set forth in the table, below. The croton oil assay procedure is described in Tonelli, et al., *Endocrinology*, 77, 625–634 (1965), incorporated herein by reference; this procedure was utilized herein except that the compositions being tested were applied 24 hours before the croton oil. In this assay, the corticosteroid-containing formulation was applied to one ear prior to inducing inflammation in both ears with a 2% croton oil application. The relative suppression of the croton oil-induced inflammation in the corticosteroid treated ear is a measure of anti-inflammatory activity. The triamcinolone acetonide + octanoic acid composition was in the form of an aqueous gel (pH=3–4) containing 1% myristyl alcohol, 25% propylene glycol, 5% Pluronic L-64, 1% beta-alanine, 25% of 4% aqueous Carbopol 934, with the balance being water. The vehicle alone, without any active components, was also tested. The following table shows the key data generated using this model system.

| Formulation | Avg. Left Ear Wt. (mg) | % Inhibition |
|---|---|---|
| 1. Croton oil (control) | 22.03 | 0 |
| 2. 0.1% Triamcinolone Acetonide + 4% Octanoic Acid (aqueous gel) | 11.32 | 97 |
| 3. Vehicle (aqueous gel) | 23.83 | 0 |
| 4. 0.1% Triamcinolone Ancetonide (aqueous gel) | — | 98 |

Formulations 2 and 4 were significantly better in their anti-inflammatory performance than the croton oil control group (P<0.05). Comparison of formulations 2 and 4 shows that there were no negative interactions regarding anti-inflammatory activity when octanoic acid was combined with Triamcinolone Acetonide. However, the aqueous gel vehicle was not significantly different from the croton oil group.

Substantially similar results are obtained where the triamcinolone acetonide contained in formulation 2 is replaced, in whole or in part, with an equivalent amount of beclomethasone dipropionate, clobetasol propionate, diflucortolone valerate, fluocinolone acetonide, betamethasone benzoate, betamethasone dipropionate, betamethasone valerate, desonide, desoxymethasone, diflorasone diacetate, fluclorolone acetonide, fluocinonide, fluocortolone, fluprednidene (fluprednylidene) acetate, flurandrenolone, halcinonide, hydrocortisone butyrate, triamcinolone acetonide, clobetasone butyrate, flumethasone pivalate, fluocortin butylester, hydrocortisone with urea, dexamethasone, hydrocortisone alcohol or acetate, methylprednisolone, or mixtures thereof.

Similar results are also obtained where the octanoic acid in formulation 2 is replaced, in whole or in part, with equivalent amounts of pentanoic, hexanoic, heptanoic, nonanoic, decanoic, undecanoic or dodecanoic acid, or mixtures thereof.

Substantially similar anti-inflammatory results are also obtained when formulation 2 is prepared as a liquid, non-aqueous gel, ointment, cream or lotion, rather than as an aqueous gel.

What is claimed is:

1. A topical pharmaceutical composition, having a pH no greater than about 5, comprising a safe and effective amount of an antimicrobial agent selected from $C_5$–$C_{12}$ fatty acids and mixtures thereof, together with a safe and effective amount of a corticosteroid component.

2. A composition according to claim 1 wherein the corticosteroid component is selected from the group consisting of beclomethasone dipropionate, clobetasol propionate, diflucortolone valerate, fluocinolone acetonide, betamethasone benzoate, betamethasone dipropionate, betamethasone valerate, desonide, desoxymethasone, diflorasone diacetate, fluclorolone acetonide, fluocinonide, fluocortolone, fluprednidene (fluprednylidene) acetate, flurandrenolone, halcinonide, hydrocortisone butyrate, triamcinolone acetonide, clobetasone butyrate, flumethasone pivalate, fluocortin butylester, hydrocortisone with urea, dexamethasone, hydrocortisone alcohol or acetate, methylprednisolone, and mixtures thereof.

3. A composition according claim 2 which contains from about 0.5% to about 20% of the antimicrobial agent.

4. A composition according to claim 3 which contains from about 0.01% to about 10% of the corticosteroid component.

5. A composition according to claim 4 which additionally contains from about 1% to about 99.5% of a pharmaceutically-acceptable topical carrier.

6. A composition according to claim 5 wherein the antimicrobial agent is selected from $C_6$–$C_{10}$ fatty acids and mixtures thereof.

7. A composition according to claim 6 wherein the antimicrobial agent is selected from octanoic acid, decanoic acid, and mixtures thereof.

8. A composition according to claim 7 wherein the corticosteroid component is selected from the group consisting of triamcinolone acetonide, hydrocortisoneacetate, betamethasone valerate, fluocinolone acetonide, and mixtures thereof.

9. A composition according to claim 8 which contains from about 1% to about 10% of the antimicrobial agent.

10. A composition according to claim 9 which contains from about 0.02% to about 5% of the corticosteroid component.

11. A composition according to claim 10 wherein the corticosteroid component is triamcinolone acetonide.

12. A composition according to claim 2 wherein the corticosteroid component is triamcinolone acetonide.

13. A composition according to claim 2 wherein the antimicrobial agent is octanoic acid.

14. A composition according to claim 2 having a pH no greater than about 4.

15. A composition according to claim 2 in the form of an aqueous gel or an aqueous lotion.

16. A method of treating inflammatory skin conditions in humans or animals comprising the topical application to the afflicted situs of a safe and effective amount of the composition according to claim 2.

* * * * *